(12) United States Patent
Mattern et al.

(10) Patent No.: US 7,883,196 B2
(45) Date of Patent: Feb. 8, 2011

(54) SYSTEM FOR DELIVERING SOLID INK THROUGH A FEED CHANNEL HAVING NON-LINEAR SECTIONS

(75) Inventors: Frederick T. Mattern, Portland, OR (US); Brent Rodney Jones, Sherwood, OR (US)

(73) Assignee: Xerox Corporation, Norwalk, CT (US)

( * ) Notice: Subject to any disclaimer, the term of this patent is extended or adjusted under 35 U.S.C. 154(b) by 522 days.

(21) Appl. No.: 12/004,846

(22) Filed: Dec. 21, 2007

(65) Prior Publication Data

US 2009/0160919 A1 Jun. 25, 2009

(51) Int. Cl.
*B41J 2/175* (2006.01)
(52) U.S. Cl. ............................ 347/88; 347/99
(58) Field of Classification Search .............. 347/88, 347/99
See application file for complete search history.

(56) References Cited

U.S. PATENT DOCUMENTS

| | | | |
|---|---|---|---|
| 4,636,803 A * | 1/1987 | Mikalsen | 347/88 |
| 5,223,860 A | 6/1993 | Loofbourow et al. | |
| 5,442,387 A | 8/1995 | Loofbourow et al. | |
| 5,734,402 A | 3/1998 | Rousseau et al. | |
| 5,861,903 A | 1/1999 | Crawford et al. | |
| 5,917,528 A * | 6/1999 | Grellmann et al. | 347/88 |
| 5,975,690 A | 11/1999 | Grellmann et al. | |
| 6,056,394 A | 5/2000 | Rousseau et al. | |
| 6,719,419 B2 | 4/2004 | Jones et al. | |
| 6,722,764 B2 | 4/2004 | Jones et al. | |
| 6,739,713 B2 | 5/2004 | Jones et al. | |
| 6,761,443 B2 | 7/2004 | Jones | |
| 6,840,613 B2 | 1/2005 | Jones | |
| 6,986,570 B2 | 1/2006 | Jones et al. | |
| 7,066,589 B2 | 6/2006 | Jones et al. | |
| 2003/0202056 A1 | 10/2003 | Jones et al. | |
| 2003/0202067 A1 | 10/2003 | Jones et al. | |
| 2003/0202069 A1 | 10/2003 | Jones | |
| 2003/0202071 A1 | 10/2003 | Jones et al. | |
| 2003/0202077 A1 | 10/2003 | Jones et al. | |
| 2003/0202078 A1 | 10/2003 | Jones et al. | |
| 2004/0179074 A1 | 9/2004 | Jones et al. | |
| 2004/0183875 A1 | 9/2004 | Jones et al. | |
| 2005/0062820 A1 | 3/2005 | Jones et al. | |
| 2005/0151814 A1 | 7/2005 | Wong et al. | |
| 2008/0136881 A1 * | 6/2008 | Fairchild et al. | 347/88 |
| 2008/0204532 A1 * | 8/2008 | Jones et al. | 347/88 |

* cited by examiner

*Primary Examiner*—Matthew Luu
*Assistant Examiner*—Rut Patel
(74) *Attorney, Agent, or Firm*—Maginot, Moore & Beck LLP

(57) ABSTRACT

A system facilitates transport of solid ink by a motorized feed drive through a feed channel in a solid ink printer. The system includes a feed channel, a motorized feed drive in at least a portion of the feed channel, a meltable ink body having a drive coupler that is offset from a surface of the meltable ink body, the drive coupler having an opening to receive a portion of the motorized feed drive to enable the motorized feed drive to urge the meltable ink body along the feed channel.

9 Claims, 2 Drawing Sheets

SYSTEM FOR DELIVERING SOLID INK THROUGH A FEED CHANNEL HAVING NON-LINEAR SECTIONS

TECHNICAL FIELD

The feed drive systems disclosed below generally relate to solid ink printers, and, more particularly, to solid ink printers that use mechanized drives to deliver solid ink sticks to a melting device in a solid ink printer.

BACKGROUND

Solid ink or phase change ink printers conventionally receive ink in various solid forms, such as pellets or ink sticks. The solid ink pellets or ink sticks are typically inserted through an insertion opening of an ink loader for the printer, and the ink sticks are pushed or slid along a feed channel by a feed mechanism and/or gravity toward a melting device. The melting device heats the solid ink impinging on the device until it melts. The liquid ink is collected and delivered to a print head for jetting onto a recording medium.

A common goal of all printers is an increase in the number of documents generated by the printer per unit of time. As the throughput of solid ink printers increase, the demand for a continuous supply of solid ink to the melting device also increases. The increased demand for solid ink has led to the development of energized drive trains for the feed mechanisms that deliver solid ink units to a melting device. For example, a lead screw, an endless belt, and other drive mechanisms may be located in a feed channel and coupled to a motor through a drive train. Selectively energizing the motor causes the drive mechanism to move and carry a solid ink unit resting on the drive towards the melting assembly. The motorized carrier more positively urges the solid ink towards the melting unit and helps maintain a continuous supply of solid ink to the melting assembly.

Previously known feed channels have included relatively planar floors to facilitate the sliding or gravitational pull on solid ink inserted into the feed channel. The incorporation of motorized drives in feed channels has typically resulted in the drive mechanism acting as the floor of the feed channel. Thus, the drive mechanisms usually contact the bottom of the solid ink along the entire length or nearly the entire length of the solid ink. As throughput for solid ink printers has increased, the dimensions of the solid ink have also increased. Consequently, longer feed channels may be used and these longer channels may have non-linear sections that accommodate the constraints of the available space within a printer.

SUMMARY

A system facilitates transport of solid ink by a motorized feed drive through a feed channel in a solid ink printer. The system includes a feed channel, a motorized feed drive in at least a portion of the feed channel, a meltable ink body having a drive coupler that is offset from a surface of the meltable ink body. The drive coupler has an opening to receive a portion of the motorized feed drive to enable the motorized feed drive to urge the meltable ink body along the feed channel.

BRIEF DESCRIPTION OF THE DRAWINGS

Features for controlling the transportation of solid ink in a solid ink printer are discussed with reference to the drawings, in which.

DETAILED DESCRIPTION

The term "printer" refers, for example, to reproduction devices in general, such as printers, facsimile machines, copiers, and related multi-function products. While the specification focuses on a system that transports solid ink through a solid ink printer, the transport system may be used with any solid ink image generating device. Solid ink may be called or referred to as ink, ink sticks, or sticks.

Figure 1:
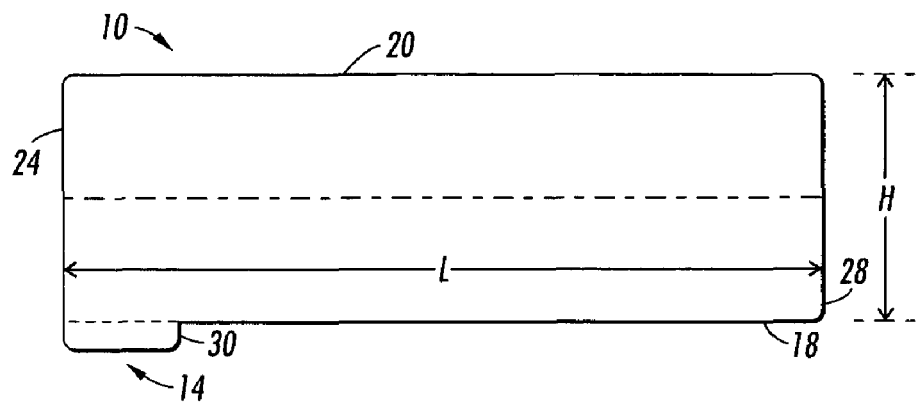
FIG. 1 is a side view of a solid ink unit having a driver coupler along a portion of the solid ink body that engages a feed drive in a feed channel.

As shown in FIG. 1, an example of a solid ink stick 10 having a drive coupler 14 is shown in a side view. The solid ink stick 10 has a meltable body with a length L and a height H, as shown in FIG. 1, and a width W, as may be seen in the front view of the stick depicted in FIG. 2. The meltable ink body of the solid ink stick 10 may have, for example, a bottom surface 18, a top surface 20, a front surface 24, and a rear surface 28, although other body shapes providing other or different surfaces may be used. The solid ink stick body has a longitudinal axis along its length L. The drive coupler 14 in the illustrated embodiment is incorporated in a portion of the bottom surface of the ink stick that is vertically displaced from the remaining portion of the bottom surface.

Figure 2:
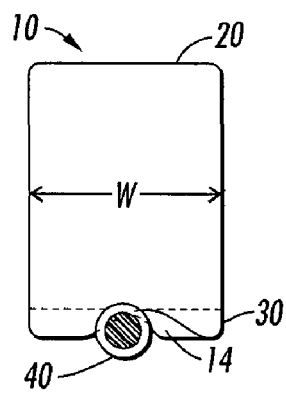
FIG. 2 is a front view of the solid ink unit shown in FIG. 1.

As shown in FIG. 1, the coupler 14 may be offset from a surface of the solid ink body, such as the bottom surface, by a coupler support 30 that extends from one of the ink body surfaces. As shown in FIG. 1, the coupler support 30 extends from the bottom surface 18. The drive coupler 14 is incorporated within the coupler support 30 (FIG. 2). The drive coupler 14 illustrated in FIG. 2 includes a semicircular opening in the coupler support 30. The coupler is configured to receive a feed drive 40 having a circular cross-sectional core area. Thus, the opening has a circular cross-section. In other embodiments, the opening of the drive coupler 14 may be square (or other rectilinear shape), V-shaped, curved, or some other shape that is useful to engage the drive mechanism. The driver coupler opening may vary in form and/or size along its length. For example, it may be round, curved, or some other shape that resembles the feed drive and then flare. The drive coupler may also have features in or along the opening, such as a "bump" or other protuberance that may increase engagement between the portion of the ink stick body from which the support 30 extends and the drive.

Figure 3:
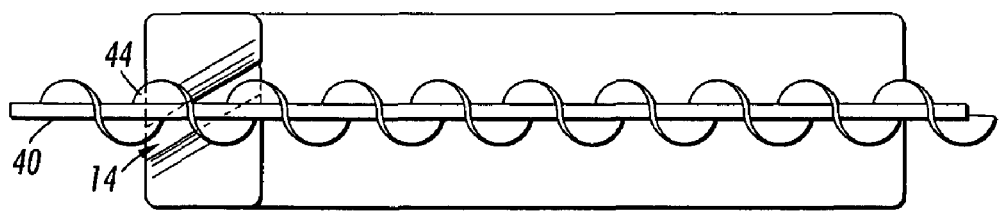
FIG. 3 is a bottom view of the solid ink unit shown in FIG. 1 showing the relationship of a leadscrew to a canted drive coupler.

In FIG. 3, the feed drive 40 is a leadscrew having a raised thread 44 that is coupled to a rotational output of a motor (not shown) and the drive coupler 14 is formed to complement the thread pitch. The rotational output of the motor may be coupled to the feed drive through a drive train to vary the speed of the screw's rotation or torque, if desired. The motor may be selectively operated to rotate the screw. In other embodiments, the feed drive may be an endless belt having, for example, a flat, elliptical, trapezoidal, circular, or other rectilinear cross-section. These types of drives may also include a protuberance extending from the drive towards the ink sticks carried by the drive. Such a protuberance may also include a slanted face that enables the ink stick to slide up and the drive to pass by the ink stick in the forward direction in response to the ink stick being stopped by a melting device or another ink stick in the feed channel. When the ink stick is not blocked in the channel, however, the protuberance more easily engages the opening of the coupler 14 to urge forward the portion of the ink stick from which the coupler support extends. Of course, the remainder of the ink stick body follows this portion.

Figure 4:
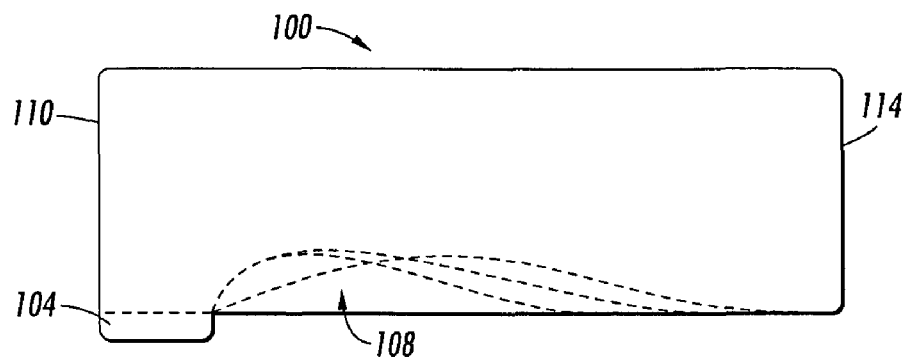
FIG. 4 is a side view of another embodiment of a solid ink unit having a solid ink body with a curved bottom surface.

As shown in FIG. 4, the opening of the drive coupler 14 may be canted at an angle to the longitudinal axis of the ink body. The angle at which the opening of the coupler is canted may be complementary to the pitch of a raised thread of the leadscrew, however, the opening may be straight in the longitudinal direction of the ink stick body depending on the screw pitch and the length of the opening. Complementary, as used in this context, means that the drive coupler does not necessarily conform to the shape of the drive identically, but rather fits the drive to facilitate engagement between the drive and the portion of the ink stick body from which the coupler support extends. An opening in the drive coupler may be contoured, for example, to match the helical form of a leadscrew or other feed drive.

The drive coupler in the illustrated embodiment enables the leadscrew to propel an ink stick through a feed channel until the stick encounters the melting device to which the solid ink is being delivered or the rear portion of another solid ink stick in the feed channel. At that point, the stick may lift slightly as the leadscrew turns and advances through the opening and past the stick since the ink cannot advance any further. As melting occurs, resistance to forward motion is reduced and the screw once again urges the ink forward in the feed channel. The specific orientation and surface depictions set forth in this description are presented to aid in understanding and visualizing the function of the drive coupler, however, the body of the ink stick may have other surface orientations as well as other longitudinal configurations. Though any orientation or feed direction is possible, pulling the stick by generating motive force closer to the front of the stick, referenced with respect to the feed direction, may be more advantageous than pushing the stick near the rear of the stick, regardless of the type of feed mechanism employed.

Figure 5:
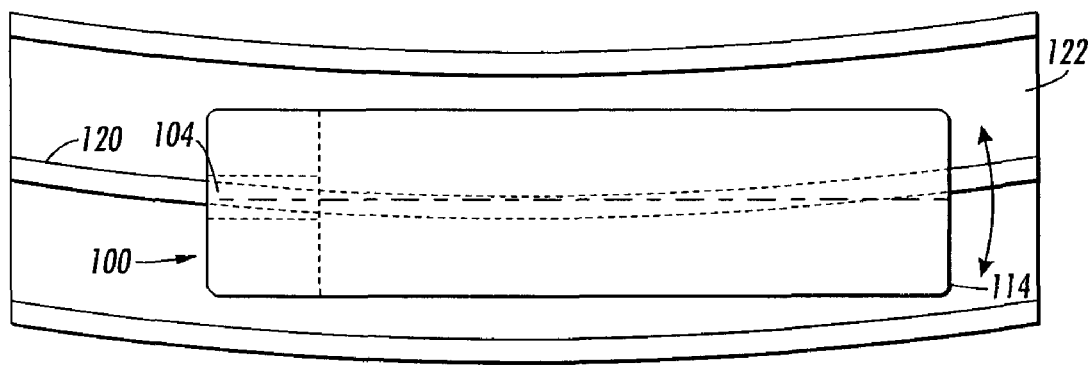
FIG. 5 is a top view of the embodiment shown in FIG. 4 negotiating a turn in a non-linear portion of a feed channel.

Another embodiment of an ink stick 100 is shown in FIG. 4 and FIG. 5. The ink stick 100 is similar to the ink stick 10 with the exception that the drive coupler is a linear relief that may be formed in a position of the ink body surface proximate the feed drive and may be formed with a radius along its top. As shown in FIG. 4, the body surface proximate the feed channel drive, which in FIG. 4 is the bottom surface 108, may be curved or in some way elevated so a portion of the surface external to the coupler support remains out of contact with the drive mechanism. Because only a portion, rather than substantially most, of the length of the ink body contacts the feed drive 120, the drive mechanism minimally influences the portion of the ink stick outside of the drive coupler. For example, as shown in FIG. 5, the curved linear relief or bottom surface that slants away from the feed drive in the longitudinal direction (FIG. 6), enables a portion of the bottom surface of the ink stick body near the rear surface 114 to move laterally through a non-linear portion of the feed channel 122 so it is not aligned or forced to track with the feed drive 120. The drive coupler 104, however, remains' engaged with the feed drive so it tracks the feed drive path more closely. Consequently, the ink stick 100 is more easily able to move through the curved channel 122 than an ink stick that has substantially the entire length of its bottom surface engaged with the feed drive 120 since the sides of the stick are not forced into contact with the feed channel walls. The same benefit extends to a vertically curved or otherwise non-linear portion of a feed channel, where the relieved portion of the surface proximate to the feed drive allows the drive coupler to remain engaged with the drive while the remainder of the ink stick body is less constrained in its movement.

Figure 6:
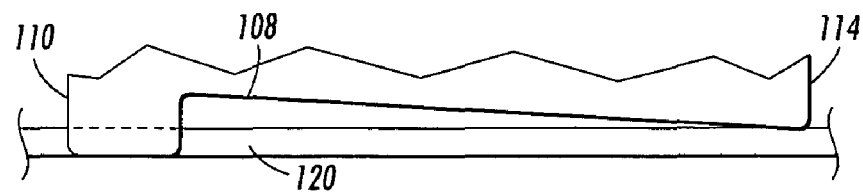
FIG. 6 is a side view of another embodiment of a solid ink unit having a solid ink body with a slanted bottom surface.

By locating the opening of the drive coupler 104 and the coupler support 108 in a portion of the surface proximate the feed drive and closer to the front of the ink stick as shown in FIG. 6, the ink stick is led by the feed drive through the feed channel without unnecessarily constraining the movement of the middle and rear portion of the ink stick along its longitudinal axis. While this type of movement may be conducive for some feed channel designs, other feed channels may be better accommodated by a drive coupler incorporated in a coupler support that extends from a surface of the ink body near the longitudinal middle of the ink stick. Locating the coupler and its support in this position enables the ink stick to rotate more freely at each end. This feature works equally well with a drive belt or conveyor that has periodic flairs or catch features (not shown). These flairs or features more positively urge the ink stick forward when feed motion is possible. They also slip under or raise the ink slightly to pass beyond the ink stick when feed motion is prevented.

Those skilled in the art will recognize that numerous modifications can be made to the specific implementations described above. Therefore, the following claims are not to be limited to the specific embodiments illustrated and described above. The claims, as originally presented and as they may be amended, encompass variations, alternatives, modifications, improvements, equivalents, and substantial equivalents of the embodiments and teachings disclosed herein, including those that are presently unforeseen or unappreciated, and that, for example, may arise from applicants/patentees and others.

The invention claimed is:

1. A system for delivering solid ink to a melting device in a solid ink printer comprising:
   a feed channel;
   a motorized feed drive having an endless belt with a rectilinear cross-section, the endless belt being in at least a portion of the feed channel;
   a meltable ink body having a drive coupler that is offset from a surface of the meltable ink body, the drive coupler having an opening to receive a portion of the endless belt to enable the endless belt to urge the meltable ink body along the feed channel.

2. The system of claim 1, the opening in the drive coupler further comprising:
   a protuberance against which a portion of the motorized feed drive pushes.

3. The system of claim 1, wherein the opening in the drive coupler is a rectilinear shape that is complementary to the rectilinear cross-section of the endless belt in the feed drive.

4. The system of claim 1, wherein the opening of the drive coupler is a linear relief in a surface of the solid ink body.

5. The system of claim 4, wherein the linear relief is curved.

6. The system of claim 4, wherein a portion of the solid ink body surface external to the coupler support is elevated to remain out of contact with the motorized feed drive in the feed channel.

7. A system for delivering solid ink to a melting device in a solid ink printer comprising:
   a feed channel;
   a motorized feed drive having an endless belt with a V-shaped cross-section, the endless belt being in at least a portion of the feed channel;

a meltable ink body having a drive coupler that is offset from a surface of the meltable ink body, the drive coupler having an opening to receive a portion of the endless belt to enable the endless belt to urge the meltable ink body along the feed channel.

8. The system of claim 7, the opening in the drive coupler further comprising:

a protuberance against which a portion of the motorized feed drive pushes.

9. The system of claim 7, wherein the opening in the drive coupler is a V-shape that is complementary to the V-shape of the endless belt cross-section.

* * * * *